United States Patent [19]

Cameron

[11] Patent Number: 4,722,837

[45] Date of Patent: Feb. 2, 1988

[54] MEDICATED SHAMPOO COMPOSITION

[75] Inventor: William W. Cameron, Chicago, Ill.

[73] Assignee: Derma-Cure, Inc., Portland, Oreg.

[21] Appl. No.: 614,814

[22] Filed: May 29, 1984

[51] Int. Cl.⁴ .................. A61K 7/06; A61K 31/095; A61K 31/59

[52] U.S. Cl. ................... 424/70; 252/106; 252/107; 424/DIG. 4; 514/26

[58] Field of Search ............... 424/70, 240, DIG. 4; 514/26

[56] References Cited

U.S. PATENT DOCUMENTS

| | | | |
|---|---|---|---|
| 2,460,776 | 2/1949 | Vincent | 424/240 |
| 2,841,527 | 7/1958 | Freedman | 424/240 |
| 2,900,307 | 8/1959 | Wei | 424/240 |
| 2,932,606 | 4/1960 | Shull et al. | 424/240 |
| 4,370,273 | 1/1983 | Kinsman | 424/70 |

FOREIGN PATENT DOCUMENTS

| | | | |
|---|---|---|---|
| 1007957 | 5/1957 | Fed. Rep. of Germany | 424/70 |
| 2219M | 12/1963 | France | 424/240 |

OTHER PUBLICATIONS

Parran et al, "The Journal of Investigative Dermatology, 8/1965, pp. 89 to 92.
Cirincione, New York State Journal of Medicine, 9/1952, vol. 52, pp. 2109–2112.
Bliss, The Drug and Cosmetic Industry, vol. 38, No. 2, 2/1936, pp. 189, 190 and 192.
Whalley, American Perfumes & Cosmetics, 8/1967, vol. 82, No. 8, pp. 47–49.
Journal of the Society of Cosmetic Chemists, 6/1961, vol. 12, No. 5, pp. 253–258, Lubowe.
Journal of the Society of Cosmetic Chemists, 3/1963, vol. 14, No. 3, pp. 135 to 145, Spoor.

*Primary Examiner*—Dale R. Ore
*Attorney, Agent, or Firm*—Robert M. Ward

[57] ABSTRACT

A medicated shampoo composition for treating scalp disorders comprising a safe and effective combination of pharmacologically active ingredients is disclosed. The active ingredients comprise between approximately 0.1% but less than approximately 0.5% by weight of a hydrocortisone in combination with between approximately 2.5% but less than approximately 5.0% by weight of colloidal sulfur disposed in an appropriate shampoo base. Preferred embodiments also include approximately 0.1% to approximately 0.5% by weight of salicylic acid as a catalyst for the colloidal sulfur and as a local mild semi-irritant.

42 Claims, No Drawings

MEDICATED SHAMPOO COMPOSITION

BACKGROUND OF THE INVENTION

The present invention is directed generally to an improved medicated shampoo composition for treating various scalp disorders or conditions. More particularly, the present application is directed to a medicated shampoo composition containing a safe and effective combination of pharmacologically active ingredients, including between approximately 0.1% but less than approximately 0.5% by weight of a hydrocortisone in combination with between approximately 2.5% but less than approximately 5.0% by weight of colloidal sulfur.

Significant proportions of the population are afflicted with various scalp disorder conditions, including but not limited to flaking, scaling, dandruff, psoriasis, eczema, seborrhea and others. In treating such conditions it is desirable to avoid sticky, gooey, gummy, greasy preparations, which may be appropriate for application to other parts of the body which may be concealed either by clothing or a bandage, as such compositions are unattractive in that they would affect the usual or normal appearance of the hair. Also, such compositions would have a tendency to rub off on anything touched by the hair. Accordingly, periodic application of an effective ingredient for treatment of such conditions in the form of a shampoo has been desirable.

In formulating a suitable combination of ingredients for treating such scalp disorder conditions, it has been necessary that such compositions be both safe and effective. Some proposed combinations of ingredients have been safe (i.e., would not cause undesirable side effects in the patient), but have not been effective against the above scalp disorder conditions. Other proposed combinations of ingredients in the prior art have made substantial progress toward treating the above scalp conditions, but have caused various undesirable side effects.

Also various proposed prior art compositions have utilized ingredients which were unstable in combination, and which led to a very short shelf life for the combined mixture. Such short shelf life has led to significant problems and has limited the channels of distribution to those of prescription medications to be produced on an individual basis. This necessary method of production for such prior art compositions has unnecessarily increased the cost to the consumer, and sometimes to prohibitive levels.

It is therefore an object of the medicated shampoo composition of the present invention to alleviate materially these disadvantages and shortcomings of the prior art.

DESCRIPTION OF THE INVENTION

The present invention comprises a medicated shampoo composition for treating scalp disorder conditions including flaking, scaling, dandruff, psoriasis, eczema, seborrhea, and other conditions. The medicated shampoo composition of the present invention includes a safe and effective combination of pharmacologically active ingredients, including between approximately 0.1% but less than approximately 0.5% by weight of a hydrocortisone in combination with between approximately 2.5% but less than approximately 5.0% by weight of colloidal sulfur. These pharmacologically active ingredients are disposed into a shampoo base. In preferred embodiments, the hydrocortisone ingredient comprises approximately 0.3% by weight. Such hydrocortisones may include:

hydrocortisone;
2-methylenehydrocortisone;
$\Delta$1-hydrocortisone;
6-methylhydrocortisone;
6-methyl-$\Delta$1-hydrocortisone;
16-hydroxy-9 fluorohydrocortisone;
16-hydroxy-9-fluoro-$\Delta$1-hydrocortisone;
the substantially water-insoluble 21-esters thereof; and/or the substantially water-insoluble 16, 21-diesters thereof.

In preferred compositions, the colloidal sulfur comprises approximately 4.0% by weight. A catalyst for the colloidal sulfur is also preferably included in the composition. Such catalyst may also act as a local mild semi-irritant. Salicylic acid is suitable for such catalyst and/or local mild semi-irritant, and may be present in amounts of approximately 0.1% to approximately 0.5% by weight.

The shampoo base of the present invention preferably comprises a detergent, with a C14-16 olefin sulfonate being generally preferred. Such detergent may be selected from the group consisting in preferred embodiments of a lauryl sulfate salt, a laureth sulfate salt, an amphoteric, and a betaine. In particular the lauryl sulfate salt may preferably comprise ammonium sulfate, sodium lauryl sulfate and TEA lauryl sulfate. The laureth sulfate salt may preferably comprise ammonium laureth sulfate, sodium laureth sulfate and TEA lauryl sulfate. The betaine may preferably comprise cocamidopopyl betaine.

The medicated shampoo composition of the present invention also preferably comprises at least one each of a foam stabilizer, foam builder, thickener, scalp coolant, shampoo stabilizer, shampoo preservative, and pH adjuster.

The foam stabilizer preferably comprises teadodecylbenzenesulfonate. The foam builder preferably comprises lauramide DEA and/or cocamide DEA. The thickener preferably comprises an inorganic salt, such as sodium chloride, ammonium chloride, potassium chloride or sodium sulfate. The scalp coolant preferably comprises a mild local irritant, such as for example menthol. The shampoo stabilizer preferably comprises PEG-120 methyl glucose dioleate. The shampoo preservative preferably comprises methylparaben and/or imidazolidinyl urea. The pH adjuster may preferably include phosphoric acid. Additionally, various fragrances and/or colorants may be added according to preference.

The following approximate range of ingredients may be utilized in preferred embodiments:

| Ingredient | Percent (by weight) |
| --- | --- |
| the hydrocortisone | 0.1%–0.5% |
| colloidal sulfur | 2.5%–5.0% |
| sulfur catalyst | 0.10%–0.5% |
| detergent | 20%–35% |
| foam stabilizer | 0.5%–2.0% |
| foam builder | 2.0%–6.0% |
| thickener | 1.0%–6.0% |
| scalp coolant | 0.5%–1.5% |
| shampoo stabilizer | 0.5%–1.5% |
| shampoo preservative | 0.1%–0.6% |
| pH adjuster | 0.1%–0.2% |
| distilled water | remainder |

-continued

| Ingredient | Percent (by weight) |
|---|---|
| | 100.0% |

PREPARATION OF THE COMPOSITIONS

EXAMPLE I

The following ingredients were combined to form the medicated shampoo of the present invention:

| | | | |
|---|---|---|---|
| 1. | methyl paraben | 6. | Salicylic Acid |
| 2. | Lauramide DEA | 7. | PEG-120 Methyl Glucos Dioleate |
| 3. | Menthol | 8. | H$_2$O |
| 4. | Hydrocortisone | 9. | Teadodecylbenzensulfonate |
| 5. | Sodium C 14–16 Olefin Sulfonate | 10. | Sodium Chloride |
| | | 11. | Imidazolidinylurea |

EXAMPLE II the above ingredients were combined according to the following mixing instructions:

A. Dissolve methylparaben in the lauramide DEA and menthol.
B. Dissolve the hydrocortisone in a portion of the sodium C olefin sulfonate and add the salicylic acid with mixing until dissolved.
C. Heat the PEG-120 methyl glucose dioleate with a small portion of the water and teadodecylbenzensulfonate until melted.
D. Dissolve the sodium chloride in a portion of the water.
E. Dissolve the imidazolidinyl urea in a small amount of water.
F. Pump the remainder of water into the mixing tank.
G. Pump the remainder of the sodium C14–16 olefin sulfonate into the tank with the water, and add (A) with controlled speed to prevent excess foaming.
H. Add (B) to the mixture of above. Add the New Sulfur W.
I. Add (C). Continue to stir. Add (E) and then (D).
J. Adjust the pH with the phosphoric acid.
K. When the formula is thoroughly mixed, add the fragrance.
L. Allow the batch to stand until foam has abated and quality control tests are performed. Then fill the bottles.

The basic and novel characteristics of the medicated shampoo compositions of the present invention will be readily understood from the foregoing disclosure by those skilled in the art. It will become readily apparent that various changes and modifications may be made in the ingredients and manner of combining said ingredients of the medicated shampoo compositions of the present invention as set forth hereinabove without departing from the spirit and scope of the invention. Accordingly, the preferred and alternative embodiments of the present invention set forth hereinabove are not intended to limit such spirit and scope in any way.

What is claimed is:

1. In a medicated shampoo composition for treating scalp disorder conditions including flaking, scaling, dandruff, psoriasis, eczema, and seborrhea, said medicated shampoo composition having a shampoo base, the improvment comprising incorporation into the shampoo composition of between approximately 0.1% but less than approximately 0.5% by weight of a hydrocortisone, in combination with between approximately 2.5% but less than approximately 5.0% by weight colloidal sulfur.

2. The medicated shampoo of claim 1 wherein said hydrocortisone comprises approximately 0.3% by weight.

3. The medicated shampoo of claim 1 wherein said colloidal sulfur comprises approximately 4.0% by weight.

4. The medicated shampoo of claim 1 further comprising a catalyst for said colloidal sulfur.

5. The medicated shampoo of claim 4 wherein said colloidal sulfur catalyst also comprises a local, mild semi-irritant.

6. The medicated shampoo of claim 4 wherein said catalyst for the said colloidal sulfur comprises salicylic acid.

7. The medicated shampoo of claim 6 wherein said salicylic acid is present in an amount of approximately 0.1% to approximately 0.5% by weight.

8. The medicated shampoo of claim 1 wherein said shampoo base comprises a detergent.

9. The medicated shampoo of claim 8 wherein said detergent comprises a C14–16 olefin sulfonate.

10. The medicated shampoo of claim 8 wherein said detergent of a lauryl sulfate salt a laureth sulfate salt, an amphoteric and a betaine.

11. The medicated shampoo of claim 10 wherein said lauryl sulfate salt is selected from ammonium lauryl sulfate, and TEA lauryl sulfate.

12. The medicated shampoo of claim 10 wherein said laureth sulfate salt is selected from the group consisting of ammonium laureth sulfate, sodium laureth sulfate, and TEA laureth sulfate.

13. The medicated shampoo of claim 10 wherein said betaine comprises cocamidopropyl betaine.

14. The medicated shampoo of claim 1 wherein said shampoo base comprises at least one foam stabilizer.

15. The medicated shampoo of claim 1 wherein said shampoo base comprises at least one foam builder.

16. The medicated shampoo of claim 1 wherein said shampoo base comprises at least one thickener.

17. The medicated shampoo of claim 1 wherein said shampoo base comprises at least one scalp coolant.

18. The medicated shampoo of claim 1 wherein said shampoo base comprises at least one shampoo stabilizer.

19. The medicated shampoo of claim 1 wherein said shampoo base comprises at least one shampoo preservative.

20. The medicated shampoo of claim 1 wherein said shampoo base comprises at least one pH adjuster.

21. The medicated shampoo of claim 14 wherein said foam stabilizer comprises teadodecylbenzensulfonate.

22. The medicated shampoo of claim 15 wherein said foam builder comprises lauramide DEA.

23. The medicated shampoo of claim 15 wherein said foam builder comprises cocamide DEA.

24. The medicated shampoo of claim 16 wherein said thickener comprises an inorganic salt.

25. The medicated shampoo of claim 24 wherein said inorganic salt is selected from the group consisting of sodium chloride, ammonium chloride, potassium chloride and sodium sulfate.

26. The medicated shampoo of claim 17 wherein said scalp coolant comprises a mild local irritant.

27. The medicated shampoo of claim 26 wherein said mild local irritant comprises menthol.

28. The medicated shampoo of claim 18 wherein said shampoo stabilizer comprises PEG-120 methyl glucose dioleate.

29. The medicated shampoo of claim 19 wherein said shampoo preservative comprises methylparaben.

30. The medicated shampoo of claim 19 wherein shampoo preservative comprises imidazolidinyl urea.

31. The medicated shampoo of claim 20 wherein said pH adjuster comprises phosphoric acid.

32. The medicated shampoo of claim 1 further comprising a fragrance.

33. The medicated shampoo of claim 14 wherein said foam stabilizer comprises in approximately 0.5%–2.0% by weight of the shampoo.

34. The medicated shampoo of claim 15 wherein said foam builder comprises approximately 2.0%–6.0% by weight of the shampoo.

35. The medicated shampoo of claim 16 wherein the thickener comprises approximately 1.0%–6.0% by weight of the shampoo.

36. The medicated shampoo of claim 17 wherein said scalp coolant comprises 0.5%–1.5% by weight of the shampoo.

37. The medicated shampoo of claim 18 wherein said shampoo stabilizer comprises 0.5%–1.5% by weight of the shampoo.

38. The medicated shampoo of claim 19 wherein said shampoo preservative comprises 0.1%–0.6% by weight of the shampoo.

39. The medicated shampoo of claim 20 wherein said pH adjuster comprises an amount of said phosphoric acid sufficient to render the pH of the shampoo in the range of approximately 3.5–6.5.

40. The medicated shampoo of claim 8 wherein said detergent comprises approximately 20%–35% by weight of the composition.

41. The medicated shampoo of claim 1 wherein said hydrocortisone is selected from the group consisting of hydrocortisone, 2-methylenehydrocortisone, $\Delta'$-hydrocortisone, 6-methylhydrocortisone, 6-methyl-$\Delta'$hydrocortisone, 16-hydroxy-9a-fluorohydrocortisone, 16-hydroxy-9a-fluoro-$\Delta'$-hydrocortisone, the substantially water-insoluble 21-esters, and the substantially water-insoluble 16,21-diesters thereof.

42. A medicated shampoo composition for treating scalp disorder conditions including flaking, scaling, dandruff, psoriasis, eczema, and seborrhea, said medicated shampoo comprising a safe and effective combination of pharmacologically active ingredients, said combination having the following formula:

| Ingredient | Percent (by weight) |
|---|---|
| a hydrocortisone | 0.1%–0.5% |
| colloidal sulfur | 2.5%–5.0% |
| sulfur catalyst | 0.10%–0.5% |
| detergent | 20%–35% |
| foam stabilizer | 0.5%–2.0% |
| foam builder | 2.0%–6.0% |
| thickener | 1.0%–6.0% |
| scalp coolant | 0.5%–1.5% |
| shampoo stabilizer | 0.5%0–1.5% |
| shampoo preservative | 0.1%–0.6% |
| pH adjuster | 0.1%–0.2% |
| distilled water | remainder |
|  | 100.0% |

* * * * *